United States Patent [19]

Eckenhoff et al.

[11] Patent Number: 4,996,060

[45] Date of Patent: * Feb. 26, 1991

[54] DEVICE COMPRISING LINER FOR PROTECTING FLUID SENSITIVE MEDICAMENT

[75] Inventors: James B. Eckenhoff, Los Altos; Judy A. Magruder, Mt. View; Richard Cortese, Cupertino; John R. Peery, Palo Alto; Jeremy C. Wright, Los Altos, all of Calif.

[73] Assignee: ALZA Corporation, Palo Alto, Calif.

[ * ] Notice: The portion of the term of this patent subsequent to Aug. 8, 2006 has been disclaimed.

[21] Appl. No.: 334,251

[22] Filed: Apr. 6, 1989

Related U.S. Application Data

[63] Continuation of Ser. No. 173,209, Mar. 25, 1988, Pat. No. 4,855,141.

[51] Int. Cl.$^5$ .............................................. A61R 9/24
[52] U.S. Cl. ..................... 424/473; 424/472; 424/468
[58] Field of Search ......................... 424/472, 473, 468

[56] References Cited

U.S. PATENT DOCUMENTS

| | | | |
|---|---|---|---|
| 2,779,241 | 6/1954 | Howard | 89/1 |
| 3,845,761 | 11/1974 | Zaffaroni | 128/130 |
| 3,845,770 | 11/1974 | Theeuwes et al. | 128/260 |
| 3,854,480 | 12/1974 | Zaffaroni | 128/260 |
| 3,865,108 | 2/1975 | Hartop | 128/260 |
| 3,896,819 | 7/1975 | Zaffaroni | 128/130 |
| 3,916,899 | 11/1975 | Theeuwes et al. | 128/260 |
| 3,995,632 | 12/1976 | Nakano et al. | 128/260 |
| 4,002,173 | 1/1977 | Manning et al. | 128/296 |
| 4,063,064 | 12/1977 | Saunders et al. | 219/121 |
| 4,077,407 | 3/1978 | Theeuwes et al. | 128/260 |
| 4,088,864 | 5/1978 | Theeuwes et al. | 219/121 |
| 4,111,202 | 9/1978 | Theeuwes | 128/260 |
| 4,111,203 | 9/1978 | Theeuwes | 128/260 |
| 4,160,020 | 1/1979 | Ayer et al. | 424/15 |
| 4,200,098 | 11/1980 | Ayer et al. | 128/260 |
| 4,203,439 | 5/1980 | Theeuwes | 128/260 |
| 4,207,893 | 6/1980 | Michaels | 128/260 |
| 4,235,236 | 11/1980 | Theeuwes | 128/260 |
| 4,285,987 | 8/1981 | Ayer et al. | 427/3 |
| 4,309,996 | 1/1982 | Theeuwes | 128/260 |
| 4,320,759 | 3/1982 | Theeuwes | 128/260 |
| 4,327,725 | 5/1982 | Cortese et al. | 128/260 |
| 4,526,938 | 7/1985 | Churchill et al. | 525/415 |
| 4,612,008 | 9/1986 | Wong et al. | 604/892 |
| 4,855,141 | 8/1989 | Eckenkoff et al. | 424/423 |

Primary Examiner—Merrell C. Cashion, Jr.
Assistant Examiner—Leon R. Horne
Attorney, Agent, or Firm—Paul L. Sabatine; Edward L. Mandell; Steven F. Stone

[57] ABSTRACT

A delivery device is disclosed for delivering a beneficial agent to an animal. The device comprises a wall housing an internal space, a beneficial agent in the space, expandable means in the space for causing the beneficial agent to be delivered from the device and means in the space for shielding the beneficial agent from fluid.

10 Claims, 4 Drawing Sheets

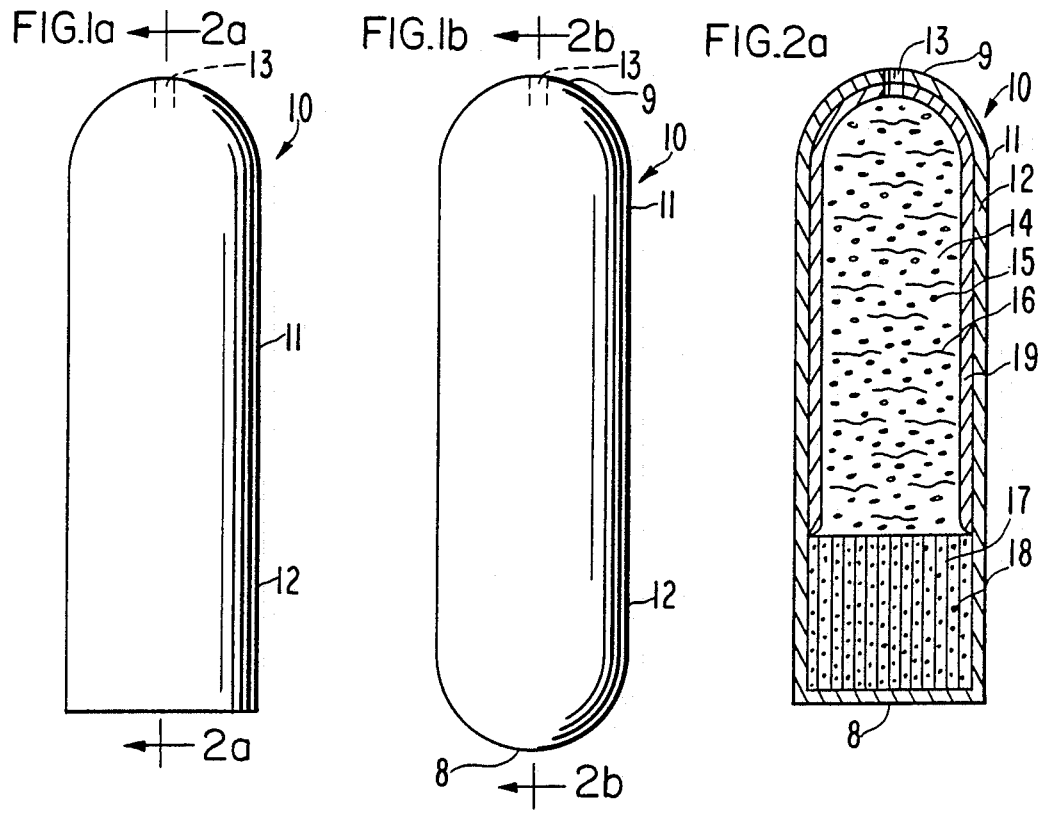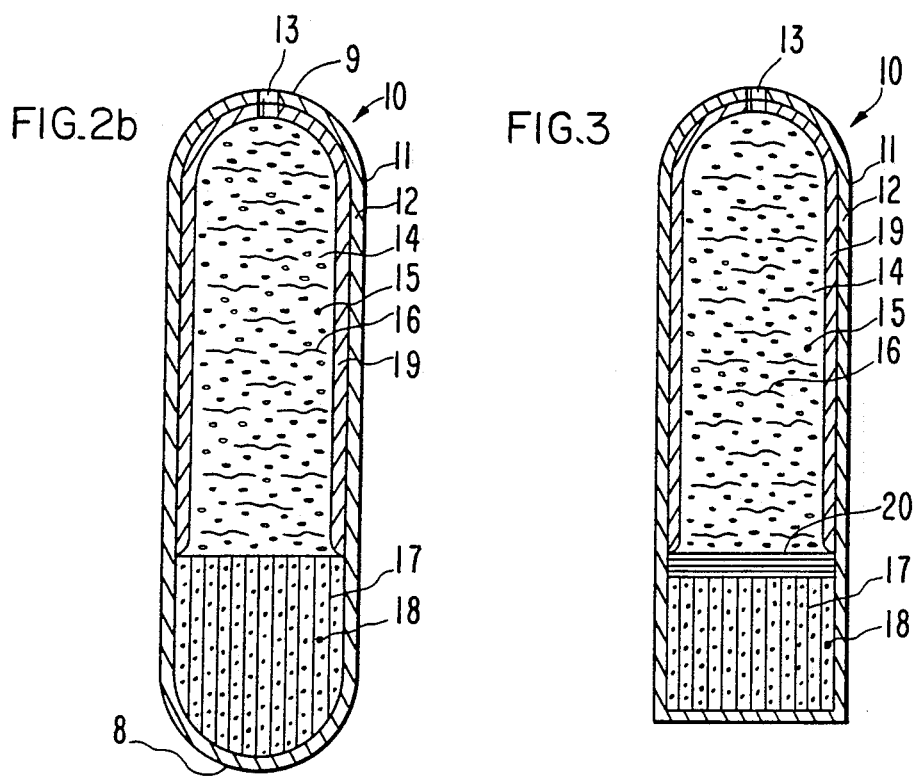

DEVICE COMPRISING LINER FOR PROTECTING FLUID SENSITIVE MEDICAMENT

CROSS-REFERENCE TO RELATED APPLICATIONS

This application is a continuation of U.S. Pat. application Ser. No. 07/173,209 filed Mar. 25, 1988, now U.S. Pat. No. 4,855,141 issued Aug. 8, 1989, and is copending with U.S. Pat. application Ser. No. 07/291,930 filed Dec. 28, 1988, U.S. Pat. No. 4,959,218. These applications are assigned to ALZA Corporation of Palo Alto, Calif., and are incorporated herein by reference and benefit is claimed of their filing dates.

FIELD OF THE INVENTION

This invention pertains to a novel and unique dispensing device. More particularly, the invention relates to a dispensing device comprising a wall permeable to the passage of fluid, which wall surrounds an internal lumen. The lumen contains (1) a bioavailable and biocompatible beneficial medicament formulation, (2) means for protecting the medicament from biological fluids, and (3) means for dispensing the medicament from the lumen. A passageway through the wall connects the exterior of the device with the lumen for releasing the medicament formulation from the dispensing device.

BACKGROUND OF THE INVENTION

Devices for delivering a beneficial agent, such as a drug, to a fluid environment of use are known to the prior art. For example, U.S. Pat. No. 3,845,770 issued to Theeuwes and Higuchi and In U.S. Pat. No. 3,916,899, issued to the same patentees, an osmotic device is disclosed comprising a semipermeable wall that surrounds a compartment containing a beneficial agent. The wall is permeable to the passage of an external fluid and there is a passageway through the wall for delivering the beneficial agent from the device. These devices release the beneficial agent by fluid being imbibed through the wall into the compartment at a rate determined by the permeability of the wall and the osmotic pressure gradient across the wall to produce an aqueous solution of the beneficial agent that is dispensed through the passageway from the device. These devices are extraordinarily effective for delivering a beneficial agent that is soluble in the aqueous fluid that exhibits an osmotic pressure gradient across the wall against the fluid. The devices are effective also for delivering a beneficial agent admixed with an osmotically effective solute that is soluble in the fluid and exhibits an osmotic pressure gradient across the wall against an aqueous fluid.

A quantum improvement in osmotic devices was presented to the pharmaceutical dispensing art by the invention Theeuwes in U.S. Pat. Nos. 4,111,202; 4,111,203 and 4,203,439. In these patents the delivery kinetics of the device were enhanced for delivering a beneficial agent with degrees of solubility in an aqueous fluid. The kinetics are improved by manufacturing the devices with a beneficial agent compartment and an osmotic compartment separated by a film. The devices deliver the beneficial agent by fluid being imbibed through the wall into the osmagent compartment producing a solution that causes the film to move and act as a driving force. This driving force pushes the beneficial agent through a passageway from the device.

A pioneer advancement in osmotic delivery devices was made by Cortese and Theeuwes in U.S. Pat. No. 4,327,725 and by Wong, Barclay, Deters and Theeuwes in U.S. Pat. No. 4,612,008. The osmotic devices disclosed in these patents comprise a semipermeable wall that surrounds a compartment. The compartment contains a beneficial agent formulation and an expandable hydrogel. In operation, fluid is imbibed into the compartment wherein it contacts the beneficial agent formulation thereby forming a dispensable formulation, and it contacts the hydrogel causing it to expand and push the dispensable formulation from the device.

The delivery devices described in the above presented patents operate successfully for their intended use and they deliver many difficult to deliver beneficial agents for their intended effect. Now, it has been observed their use can be limited because beneficial agents that are sensitive to aqueous biological fluids, or other fluid external to the delivery device, may be adversely effected by fluid imbibed into the compartment that contacts the beneficial agent during operation of the device. Examples of such sensitive agents include proteins and peptides.

It will be appreciated by those versed in the dispensing art that if a delivery device is provided for delivering a beneficial agent sensitive to aqueous fluids at a controlled rate, such a device would have a positive value and represent an advancement in the dispensing art. Likewise, it will be immediately appreciated by those versed in the dispensing art that if a delivery device is made available comprising means for protecting an aqueous sensitive beneficial agent, and which device possesses the thermodynamic ability to deliver the protected beneficial agent at a controlled rate, such a device would have a practical application in the fields of human and veterinary medicine.

OBJECTS OF THE INVENTION

Accordingly, it is an immediate object of this invention to provide a delivery device for delivering a beneficial agent and which delivery device overcomes the limitations associated with the prior art.

Another object of this invention is to provide a delivery device that can be manufactured by standard manufacturing techniques into various sizes, shapes and forms that represent a further improvement and advancement in the dispensing art.

Another object of the invention is to provide a delivery device for delivering in vivo a beneficial agent such as a drug that is difficult to deliver and now can be delivered by the device in therapeutically effective amounts.

Another object of the invention is to provide a delivery device comprising means for protecting a beneficial agent such as a drug from aqueous type fluids.

Another object of the invention is to provide a delivery device comprising means for protecting an aqueous sensitive beneficial agent from an aqueous fluid and means for delivering the beneficial agent to an environment of use, where the environment of use may be aqueous.

Another object of the invention is to provide a delivery device comprising means for storing and protecting a bioactive beneficial agent formulated in a biocompatible composition during its residency in the delivery device.

Another object of the invention is to provide a delivery device comprising means for protecting a beneficial agent formulation from a fluid present in the environment of use and for delivering the beneficial agent formulation from the device.

Another object of the invention is to provide a delivery device comprising means for high loading of a beneficial agent essentially free from inactivation while in the device, and means for delivering the beneficial agent at a controlled rate and continuously over time to a beneficial agent recipient.

Another object of the invention is to provide a delivery device manufactured as an osmotic therapeutic device that can administer a complete pharmaceutical dosage regimen comprising a beneficial agent at a controlled rate and continuously for a particular time period, the use of which requires intervention only for the initiation and possibly for the termination of the regimen.

Still a further object is to provide a delivery device manufactured as an osmotic device that possesses the ability to deliver a beneficial drug over a broad range of dosage delivery rates according to a predetermined drug timed release pattern to a biological recipient over time.

Another object of the invention is to provide an osmotic device that is useful for delivering a drug that is difficult to deliver and can be delivered by the subject device at meaningful therapeutic rates over time.

Another object of the invention is to provide a device for delivering a drug to an animal, including cattle, swine and pigs, over time.

Still another object of the invention is to provide an osmotic device comprising a compartment containing a drug shielded from a fluid environment of use, and an expandable driving member that operates to diminish the volume available to be occupied by the drug, thereby delivering the drug from the device at a controlled rate over time.

Yet another object of the invention is to provide an osmotic device having a compartment housing a fluid sensitive drug shielded from a fluid environment of use, and an expandable driving member made of a hydrogel, and which hydrogel can continuously increase in volume and generate a force that correspondingly acts to decrease the volume occupied by the drug for dispensing the drug from the device.

Another object of the invention is to provide a delivery device for delivering a dosage unit amount of a drug to a warm-blooded animal, such as a ruminant, swine and pigs, and which delivery device can be shaped, sized and adapted as an implant for implanting in the muscle tissue of the animal.

Another object of the invention is to provide a drug delivery device that is implantable, is compact in size and shape to allow easy placement within the lumen of trocars and similar implanting or injecting instruments that are limited dimensions and, consequently, are essentially free of undue trauma and discomfort to a receiving animal.

Another object of the invention is to provide a delivery device shaped at the ends in a conical or spherical shape for reducing the force necessary to push the device into the implantation receiving site, thereby reducing the incidence of tissue damage and the incidence of damage to the delivery device, and enhancing the process of implantation.

Another object of the invention is to provide a delivery device comprising ends in a conical or spherical shape for producing a device better designed to withstand elevated interior pressures occurring within the device during pumping, which shape is of value when the device is delivering high viscosity compositions that create higher pressure during pumping at given flow rates and exit sized passageways.

Other objects, features and advantages of the invention will be more apparent to those versed in the dispensing art from the following detailed specification taken in conjunction with the accompanying claims.

BRIEF DESCRIPTION OF THE DRAWINGS

In the drawing figures, which are not drawn to scale but are set forth to illustrate various embodiments of the invention, the drawing figures are as follows:

FIG. 1a is a delivery device provided by the invention for delivering a beneficial agent to a fluid environment of use;

FIG. 1b is a delivery device provided by the invention for delivering a beneficial agent formulation, which delivery device is similar to the delivery device of FIG. 1a with the added embodiment that the delivery device comprises a dome-shaped bottom;

FIG. 2a is an opened view of the delivery device of FIG. 1a, illustrating one structural embodiment of the invention;

FIG. 2b is an opened view of the delivery device, which delivery device is like the delivery device of FIG. 2a with the added structure comprising a hemispherical end;

FIG. 3 is an opened view of the delivery device of FIG. 1a, illustrating another structural embodiment of the invention;

In the drawings and in the specification like parts in related figures are identified by like parts. The terms appearing earlier in the specification and in the description of the drawings, as well as embodiments thereof, are further detailed elsewhere in the disclosure.

DETAILED DESCRIPTION OF THE DRAWING FIGURES

Figure 4:
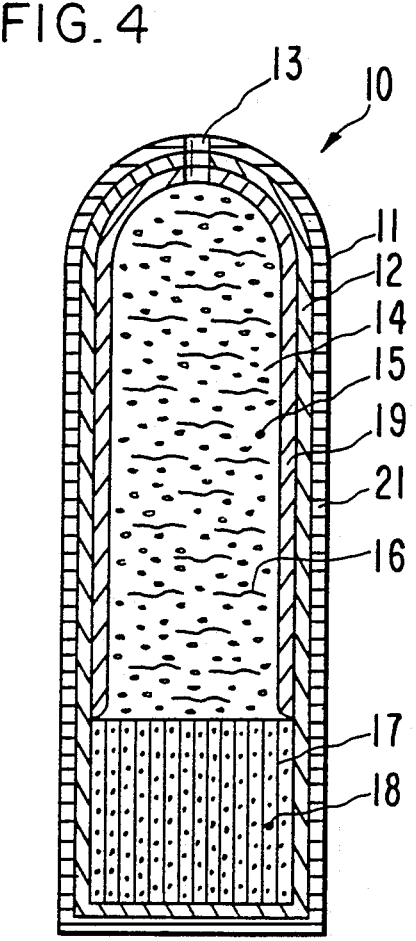
FIG. 4 is an opened view of the delivery device depicting the device with an outside coat in contact with a middle positioned wall.

Turning now to the drawings in detail, which are examples of various delivery devices provided by the invention and which examples are not to be construed as limiting, one example of a delivery device is seen in FIG. 1a and in FIG. 1b as indicated by the number 10. In FIG. 1a, delivery device 10 comprises body 11 formed of wall 12, which wall 12 surrounds and defines an internal lumen, not seen in FIG. 1a. Therapeutic delivery device 10 comprises at least one passageway 13, indicated by a partial hole, for delivering a beneficial agent formulation from delivery device 10. In FIG. 1b, delivery device 10 comprises a body 11 comprising wall 12, which wall surrounds and forms an internal lumen, not seen in FIG. 1b. Delivery device 10 comprises at least one passageway 13 for delivering a beneficial agent formulation from delivery device 10. In FIG. 1b, delivery device 10 comprises a dome-shaped end 8 similar to lead end 9 for aiding in placing delivery device 10 in an animal host. In an embodiment not seen, device 10 can be manufactured with a pan of flat ends 8 and 9.

FIG. 2a and FIG. 2b depict an opened view of delivery device 10 of FIG. 1a and FIG. 1b through 2—2 of device 10. Therapeutic delivery device 10 of FIG. 2a comprises body 11, wall 12, lead end 9, trailing end 8 and passageway 13. Wall 12 surrounds and defines an internal lumen 14, also defined as internal compartment 14. In a presently preferred embodiment wall 12 is formed at least in part of a semipermeable wall forming composition that is permeable to the passage of fluid and it is substantially impermeable to the passage of a beneficial agent and other ingredients contained in delivery device 10. Wall 12 optionally comprises additional wall forming compositions such as a polymeric means for increasing or for decreasing the permeability of wall 12 to the passage of fluid, and a plasticizer that imparts flexibility and workability to wall 12. Wall 12 is non-toxic and it maintains its physical and chemical integrity, that is, wall 12 doesn't erode during the dispensing period.

Lumen 14 contains a first composition comprising a beneficial agent 15, identified by dots, and a pharmaceutically acceptable biocompatible carrier 16, identified by wavy lines. Lumen 14 further contains a second composition comprising an expandable driving member 17, identified by vertical lines, and an optional osmagent 18; identified by dots, homogeneously or heterogeneously blended with means 17. In the embodiment illustrated the first composition comprising beneficial agent 15 and pharmaceutically acceptable biocompatible carrier 16, and the second composition comprising expandable driving member 17, are in layered contact through a contacting surface of each composition. Both the first composition and the second composition generally comprise a shape that initially corresponds to the internal shape of lumen 14.

Lumen 14 also contains means 19 for substantially protecting a beneficial agent 15 that is sensitive to fluid from an exterior fluid present in the environment of use. Means 19 comprises a material that is substantially impermeable to the passage of fluid and it prevents fluid that passes through wall 12 from entering lumen 14 in the region protected by means 19. Means 19 in the embodiment illustrated is in contact with the internal surface of wall 12. Means 19 is designed and adapted, in one embodiment, as a sleeve or an internal liner and it contacts and covers the internal surface area occupied initially by the first composition. In another embodiment, means 19 is a coating comprising a composition substantially impermeable to the passage of aqueous and biological fluids. Means 19 applied as a coat on the internal surface of wall 12, coats the internal surface area occupied by the beneficial agent composition.

Delivery device 10 comprises at least one passageway, or more than one passageway, for connecting internal compartment 14 with the exterior of device 10. Passageway 13 extends through wall 12 and means 19 for delivering beneficial agent composition 15 from internal lumen 14.

FIG. 2b depicts delivery device 10 in opened-longitudinal section. Device 10, in FIG. 2b, comprises body 11, wall 12, lumen 14; passageway 13, lead end 9, and trailing end 8. Lead end 9 and trailing end 8 can be double hemisphere, double conical, or like shaped ends. Optionally lead end 9 and trailing end 8 can be flat. Device 10 can comprise mixed ends also, such as a hemispherical lead end 9 and a flat trailing end 8. Device 10 of FIG. 2b also comprises first composition 15, pharmaceutically acceptable carrier 16, expandable driving means 17, optional osmagent 18 and fluid restricting means 19.

FIG. 3 is an opened section view of delivery device 10 illustrating another embodiment provided by the invention. In FIG. 3, delivery device 10 comprises a body 11 comprising wall 12 that surrounds a compartment 14. Compartment 14 comprises a first composition and a second composition. The first composition comprises a beneficial agent 15 and a pharmaceutically acceptable carrier 16, and the second composition comprises a driving means 17 and an optional osmotically effective solute 18. Compartment 14 also contains a means 19 that surrounds the first composition, which means 19 prevents external fluid from passing into the first composition. Means 19 is selected from the group consisting of a fluid impermeable liner and a liquid impermeable coat. At lease one passageway 13 connects the exterior of device 10 with the first composition for delivering the beneficial agent 15 to a biological receptor site. Delivery device 10 as seen in FIG. 3 comprises, additionally, a layer 20 positioned between the first composition and the second composition. Layer 20 comprises a composition that is substantially impermeable to the passage of fluid and it serves to prevent the passage of fluid present in the second composition from passing into the first composition. Layer 20 acts also to insure that expanding driving forces generated by the second composition are applied directly against the first composition. In operation, as the second composition expands it pushes against layer 20 that slides along means 19 toward passageway 13 for maximizing the delivery of beneficial agent 15 through passageway 13 to a biological environment of use, such as farm livestock.

FIG. 4 is an opened view of delivery device 10 illustrating another embodiment provided by the invention. In FIG. 4, delivery device 10 comprises body 11, which body 11 comprises wall 12 that surrounds a compartment 14 containing a first composition and a second composition. The first composition comprises beneficial agent 15 and a pharmaceutically bioacceptable, non-toxic carrier 16 for beneficial agent 15. The second composition comprises a hydrophilic driving means 17 and an optional osmotically effective compound 18, also known as an osmagent. Compartment 14 contains also a means 19 formed of a material that is very poorly permeable to impermeable to the passage of fluid, and which means 19 surrounds the first composition. A passageway 13 connects the exterior of device 10 with compartment 14 for delivering beneficial agent 15 to a biological environment of use. Delivery device 10, as seen in FIG. 4, comprises, additionally, an outermost coat 21 that is in contact with the exterior surface of wall 12. Coat 21 comprises at least in part a semipermeable composition permeable to the passage of fluid and it acts as a means for additionally regulating the passage of fluid through wall 12. Coat 21 imparts also additional strength to delivery device 10 for maintaining the structural integrity of device 10 during its drug delivery period.

Figure 5:
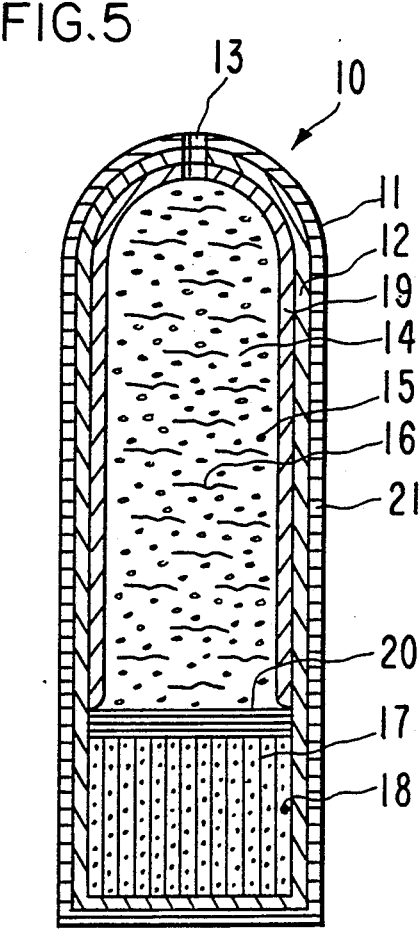
FIG. 5 is an opened view of the delivery device of FIG. 4, illustrating an embodiment of the invention wherein the device comprises a layer impermeable to the passage of fluid positioned between a first and second composition.

FIG. 5 is an opened view of delivery device 10 depicting another structure provided by the invention. In FIG. 5, delivery device 10 comprises, in combination, the structural embodiments depicted in FIGS. 3 and 4. Delivery device 10 in FIG. 5 comprises body 11, middle wall 12, passageway 13, compartment 14, beneficial agent 15, pharmaceutically acceptable carrier 16, driving means 17, optional osmagent 18, interior fluid impermeable means 19, fluid and drug impermeable layer 20, and exterior coat 21.

The delivery devices of FIGS. 1 through 5 can be manufactured for delivering numerous beneficial agents, including drugs, at a controlled rate to a presently preferred biological environment of use, such as a warm-blooded animal, including humans. The delivery device provides also for the high loading of a beneficial agent, and for its delivery in therapeutically effective amounts over time. FIGS. 1 through 5 are illustrative of various delivery devices that can be made according to the invention. In one presently preferred manufacture the device is made with a cylinder shape with hemisphere ends. In another preferred manufacture device 10 is made with conical ends for ease of implantation in a subcutaneous space. It is additionally to be understood these devices are not to be construed as limiting, as the delivery devices can take a wide variety of shapes, sizes and forms adapted for delivering beneficial agents to an environment of use. For example, the delivery devices include analrectal, artificial glands, buccal, cervical canal, implant, intrauterine, muscle, oral, ruminal, sublingual, subcutaneous, vaginal, and the like. The devices can be used in hospitals, nursing homes, outpatient clinics, veterinary clinics, sickrooms, farms, zoos, and other environments of use.

DETAILED DESCRIPTION OF THE INVENTION

In accordance with the practice of this invention it now has been found that delivery device 10 can be manufactured with a wall 12 that surrounds a compartment 14 comprising a first composition and a second composition. Wall 12 comprises materials that do not adversely affect the beneficial agent, the osmagent, the osmopolymer, the host, and the like. Wall 12 comprises a semipermeable composition that controls fluid flux. In another preferred embodiment wall 12 comprises at least in part a semipermeable composition that controls fluid flux, with the remaining part substantially impermeable to the passage of fluid. Wall 12 in another embodiment comprises a semipermeable material and means for aiding in regulating the fluid flux of wall 12. In an optional embodiment, wall 12 comprises a plasticizer for imparting manufacturing properties to wall 12. The semipermeable material is permeable to the passage of external fluids such as water and biological fluids, and it is substantially impermeable to the passage of beneficial agents, osmagents, osmopolymers, and the like. Typical semipermeable materials for forming wall 12 are, in one presently preferred embodiment, a member selected from the group consisting of a cellulose ester, a cellulose ether and a cellulose ester-ether. These cellulosic polymers have a degree of substitution, D. S., on the anhydroglucose unit, from greater than 0 up to 3, inclusive. By degree of substitution is meant the average number of hydroxyl groups originally present on the anhydroglucose unit comprising the cellulose polymer that are replaced by a substituting group. Representative materials include, but are not limited to, a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary cellulosic polymers include cellulose acetate having a D. S. up to 1 and an acetyl content up to 21%; cellulose acetate having an acetyl content of 32% to 39.8%; cellulose acetate having a D. S. of 1 to 2 and an acetyl content of 21% to 35%; cellulose acetate having a D. S. of 2 to 3 and an acetyl content of 35% to 44.8%, and the like. More specific cellulosic polymers include cellulose propionate having a D. S. of 1.8 and a propionyl content of 39.2% to 45% and a hydroxyl content of 2.8% to 5.4%; cellulose acetate butyrate having a D. S. of 1.8, an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose acetate butyrate having a D. S. of 1.8, an acetyl content of 4% average weight percent and a butyryl content of 51%; cellulose triacylates having a D. S. of 2.9 to 3 such as cellulose trivalerate, cellulose trilaurate, cellulose tripalmitate, cellulose trisuccinate, and cellulose trioctanoate; cellulose diacylates having a D. S. of 2.2 to 2.6 such as cellulose disuccinate, cellulose dipalmitate, cellulose dioctanoate, cellulose dipentate; coesters of cellulose such as cellulose acetate butyrate and cellulose acetate propionate, and the like. The amount of semipermeable material presently preferred in wall 12 is about 40% to 90%.

Representative materials used to further regulate the fluid flux of wall 12 include materials that decrease the fluid flux and materials that increase the fluid flux of wall 12. Materials added to wall 12 for decreasing the flux comprise a member selected from the group consisting of a polyacrylate; polymethacrylate; polysulfone; polyacrylic ester; polyacrylonitrile; polycarbonate; polyacrylamide; polystyrene; polyamide; polycaprolactam; polyhexamethylene adipamide; polyhexamethylene sebacamide; polyepoxyde; polyformaldehyde, and the like. Materials that increase the permeability of wall to the passage of exterior fluid include polyvinyl alcohol; poly(1,4-anhydro-beta-D-mannuronic acid); polyesters derived from the condensation of a polyhydric alcohol and a polyfunctional acid wherein the functionality refers to reactive groups such as hydroxyl, carboxyl and the like; polysaccharides; hydroxy alkylcellulose having a molecular weight from 9,000 to 35,000; polyalkylene glycol, and the like. The concentration of means for regulating the flux in wall 12 is about 5% to 50%.

The fluid flux through a wall forming polymeric material can be measured by techniques known to the art. One technique that has been found to be eminently well suited is to cast or hot press a film of the material to a thickness in the rate of 1 to 60 mils. The film is used as a barrier between a fluid source and a container initially free of fluid. Then, by measuring the volume of fluid that passed through a film of known area and thickness, the flux is easily ascertained by standard techniques known to the art as recorded in *J. Pharm. Sci;* Vol. 52, pp 1145–49 and ibid., Vol. 53, pp 798–802, (1964); ibid., Vol. 54, pp 1459–64, (1965); ibid., Vol. 55, pp 840–43 and pp 1224–39, (1966)., *Encycl. Polymer Sci. Technol.,* Vols. 5 & 9, pp 65–82 and 794–807, (1968), and the references cited therein; in U.S. Pat. Nos. 3,845,480; 3,845,761 and 3,896,819. Walls that exhibit a fluid permeability of $10^{-6}$ to $10^{-1}$ (cc.mil/cm$^2$.hr atm) can be used for the purpose of this invention. The polymers are known to the art in the *Handbook of Common Polymers,* by J. R. Scott and W. J. Roff, (1971), published by CRC Press, Cleveland, Ohio.

Wall 12 optionally comprises a non-toxic plasticizer. Representative plasticizers suitable for forming wall 12 include plasticizers that lower the temperature of the second-order phase transition of wall 12, or the elastic modules of wall 12; also, the plasticizer increases the workability of wall 12 and its flexibility. Plasticizers operable for the present purpose include straight chain and branched plasticizers, cyclic plasticizers, acrylic plasticizers and heterocyclic plasticizers. Representative plasticizers include a member selected from the group consisting of phthalate, phosphate, citrate, adipate, tartrate, sebacate, succinate, glycolate, glycerolate, benzoate, myristate, sulfonamide and halogenated plasticizer. Generally wall 12 will comprise from 1% to 35% plasticizers or more, with the total concentration of all ingredients in wall 12 equal to 100%.

Representative plasticizers include dialkyl phthalate, dicycloalkyl phthalate, diaryl phthalate, dimethyl phthalate, dipropyl phthalate, di(2-ethylhexyl) phthalate, di-isopropyl phthalate, alkyl phosphate, aryl phosphate, tributyl phosphate, trioctyl phosphate, tricresyl phosphate and triphenyl phosphate; alkyl citrate, citrate esters, tributyl citrate, triethyl citrate and acetyl triethyl citrate; alkyl adipates such as dioctyl adipate, diethyl adipate and di(2-methoxyethyl)-adipate; dialkyl tartrates such as diethyl tartrate, and butyl tartrate; alkyl sebacates such as diethyl sebacate, dipropyl sebacate and dinonyl sebacate; alkyl succinates such as diethyl succinate and dimethyl succinate; alkylglycolates, alkyl glycerolates, glycol esters and glycerol esters such as glycerol diacetate, glycerol triacetate, glycerol monolactate diacetate, methyl phythayl ethyl glycolate, and the like.

Suitable plasticizers can be selected for blending with the wall forming materials by selecting plasticizers that have a high degree of solvent power for the materials, are compatible with the materials over both the processing and use temperature range, exhibit permanence as seen by its strong tendency to remain in the plasticized wall, but in storage and in the biological environment of use, imparts flexibility to the material, and are non-toxic to animals, humans, avians, fishes and reptiles. Procedures for selecting a plasticizer having the described characteristics are disclosed in the *Encyclopedia of Polymer Sciences and Technology*, Vol. 10, pp 118–306, (1969), published by John Wiley & Sons, Inc. Also, a detailed description pertaining to the measurement of plasticizer properties including solvent parameters and compatibility, such as the Hildebrand solubility perameter $\delta$, the Flory-Huggins interaction parameter $\mu$, and the cohesive-energy density, CED, parameters are disclosed in "Plasticization and Plasticizer Processes," *Advances in Chemistry Series* 48, Chapt. 1, pp 1–26, (1965), published by the American Chemical Society, and in U.S. Pat. No. 4,077,407.

The inner means 19, when manufactured as a liner or sleeve, comprises a polymeric composition that substantially restricts or totally prevents the passage of an exterior fluid that is present in the environment of use into compartment 14. Polymeric materials useful for forming liner 19 comprise olefin polymers, vinyl polymers, addition polymers, condensation polymers, coactivation polymers, coordination polymers, and rubber polymers. Representative polymers include fluid restricting polyethylene, polytetrafluroethylene, polycarbonate, polystyrene, polyamide, polyformaldehyde, polymelamine formaldehyde, polysulfone, styrene butadrene rubber, fluid impermeable polyurethane, polypropylene, polyvinyl chloride, and the like. The same materials optionally can be used when means 19 is applied as an interior coat. The coat can be applied using organic solvents that are vacuum stripped from the coat to leave a dry coat. The permeability of water through a polymer used for manufacturing means 19, which is a fluid barrier, can be ascertained by following the techniques disclosed in *Handbook of Common Polymers*, by J. R. Scott and W. J. Roff, Section 64, published in 1971 by CRC Press, Cleveland, Ohio.

Coat 21, in laminated contact with outermost surface of wall 12, comprises a selectively semipermeable material that is insoluble in fluid present in the environment of use and is non-erodible. Coat 21, in a presently preferred proviso, comprises a composition that is different than the composition comprising wall 12. Coat 21 comprises semipermeable polymers known to the art as osmosis and reverse osmosis polymers. The semipermeable polymers useful for forming coat 21 comprise a member selected from the group consisting of cellulose acylate, cellulose diacylate, cellulose triacylate, cellulose acetate, cellulose diacetate, cellulose triacetate, cellulose acetate ethylcarbamate, cellulose acetate butyrate, semipermeable polyamide, semipermeable polyurethane, cellulose acetate succinate, cellulose acetate chloroacetate, cellulose acetate dipalmatate, cellulose dicaprytate, cellulose acetate valerate, cellulose-acetae propionate, cellulose propionate succinate, and the like. Semipermeable polymers operable for forming coat 21 are known to the prior art in U.S. Pat. Nos. 3,133,133; 3,845,770; 3,916,899; 4,160,020; 4,327,725 and 4,612,008.

The first composition in compartment 14 comprises beneficial agent 15 and presently preferred pharmaceutically acceptable carrier 16. Beneficial agent 15, in one embodiment, is a drug useful for producing a therapeutic effect. Typical drug 15 that can be administered by the delivery device provided by the invention comprise drugs acting as synaptic and neuroeffector sites, drugs acting on the central nervous system, autocoids, anti-inflammatory, analgesic, antipyretic, cardiovascular drugs and the like. The drugs in a presently preferred embodiment include drugs that produce a therapeutic effect in animals including humans, such as peptides and protein drugs, growth hormones, somatropin, somatotropin, gonadotropic hormones, follicle stimulating hormone, luteinizing hormone, gonadotropin, insulin, colchicine, chorionic gonadotropin, cosyntropin, lypressin, vasopressin, polypeptides such as thyrotropin releasing hormone, thyroid stimulating hormone, oxytocin, secretin, pancreozymin, enkephalin, and the like. The drugs and their dosage unit amount are known to the prior art in *The Pharmacological Basis of Therapeutics*, by Gilman, Goodman, Rall and Murad, 7th Ed., (1985), published by MacMillan Publishing Co., NY; and in *Pharmaceutical Sciences*, Remington, 17th Ed., (1985), published by Mack Publishing Co., Easton, Penna.

The pharmaceutically acceptable carrier 16 comprises a fluid member and a gelling member. The fluid member in a presently preferred embodiment comprise a polyol such as a diol, triol, polyhydric alcohols, and the like. More specific polyols include 1,5 pentylene glycol; 1,6-hexylene glycol; 1,7-heptylene glycol; 1,9-nonylene glycol; 1,2-dimethyl-1,6-hexylene glycol; 1,2,3,-propanetriol; 1,2,5-pentanetriol; 1,3,5-pentanetriol; 1,2,4-butanetriol; dipentaerythriol, and the like. The gelling agent homogeneously blended with the fluid carrier member includes a member selected from the group consisting of gelatin, such as gelatin prepared from porcine skin, gum tragaconth, gum acacia, gum karaya, polysuccrose, polyglucose, pectin, sodium alginate, polyvinyl alcohol, hydroxyethyl cellulose, and the like. Generally the pharmaceutically acceptable carrier composition in one preferred embodiment, comprises from 40% to 75% fluid, from 0.1% to 20% gelling member and from 10% to 50% beneficial drug, with the total for all components 100%; and in another preferred embodiment the pharmaceutically acceptable carrier composition comprises from 40% to 75% fluid member, from 0.1% to 20% gelling member, from 15% to 50% beneficial drug and from 5% to 15% water, with the total of all components equal to 100%. In another preferred embodiment the pharmaceutically acceptable carrier composition comprises from 40% to 75% fluid member, 20% to 40% of a physiologically acceptable buffer/diluent and 10% to 50% beneficial drug, with the total for all components 100%. In an optional embodiment means for protecting the drug can be added to the first composition, usually from 0.1% to 5%, with the total of all ingredients in the composition 100%. Pharmaceutically acceptable carrier members are known in EPO 0 094 157, and in *Pharmaceutical Sciences* by Remington, 14th Ed., (1970), published by Mack Publishing Co., Easton, Penna.

The driving member 17, operable for pushing the first composition from delivery device 10, comprises a swellable hydrophilic polymer. Hydrophilic polymers are known also as osmopolymers. The osmopolymers interact with water and aqueous biological fluids and swell or expand to an equilibrium state. The osmopolymers exhibit the ability to swell in water and retain a significant portion of the imbibed water within the polymer structure. The osmopolymers swell or expand to a very high degree, usually exhibiting a 2 to 50 fold volume increase. The osmopolymers can be noncross-linked or cross-linked. The swellable, hydrophilic polymers are, in one presently preferred embodiment, lightly cross-linked, such as cross-links being formed by covalent or ionic bonds. The osmopolymers can be of plant, animal or synthetic origin. Hydrophilic polymers suitable for the present purpose include poly(hydroxyalkylmethacrylate) having a molecular weight of from 30,000 to 5,000,000; poly(vinylpyrrolidone) having molecular weight of from 10,000 to 360,000; anionic and cationic hydrogels; polyelectrolyte complexes, poly(vinyl alcohol) having a low acetate residual, cross-linked with flyoxal, formaldehyde, or glutaraldehyde and having a degree of polymerization from 200 to 30,000; a mixture of methyl cellulose, cross-linked agar and carboxymethyl cellulose; a water insoluble, water swellable copolymer reduced by forming a dispersion of finely divided copolymer of maleic anhydride with styrene, ethylene, propylene, butylene or isobutylene cross-linked with from 0.0001 to about 0.5 moles of polyunsaturated cross-linking agent per mole of maleic anhydride in the copolymer; water swellable polymers of N-vinyl lactams, and the like.

Other osmopolymers include polymers that form hydrogels such as Carbopol ® acidic carboxy polymers generally having a molecular weight of 450,000 to 4,000,000; the sodium salt of Carbopol ® acidic carboxy polymers and other metal salts; Cyanamer ® polyacrylamides; cross-linked water swellable indene-maleic anhydride polymers, Goodrite ® polyacrylic acid having, but not limited to, a molecular weight of 80,000 to 200,000, and the sodium and other metal salts; Polyox ® polyethylene oxide polymers having a molecular weight of 100,000 to 4,000,000; starch graft copolymers; Aqua-Keeps ® acrylate polymers; diester cross-linked polyglucan, and the like. Representative polymers that form hydrogels are known to the prior art in U.S. Pat. No. 3,865,108 issued to Hartop; U.S. Pat. No. 4,002,173 issued to Manning; U.S. Pat. No. 4,207,893 issued to Michaels, and in *Handbook of Common Polymers*, by Scott and Roff, published by the Chemical Rubber, CRC Press, Cleveland, Ohio.

The second composition comprising driving osmopolymer 17 can comprises an additional osmagent 18. Osmagents are known also as osmotically effective solutes and as osmotically effective compounds. The osmotically effective compounds that can be used for the purpose of this invention include inorganic and organic compounds that exhibit an osmotic pressure gradient across the semipermeable wall 12. The osmotically effective compounds, along with the osmopolymers, imbibe fluid into the device thereby making available in situ fluid for imbibition by an osmopolymer to enhance its expansion. The osmotically effective compounds are used by mixing them with the osmopolymer, homogeneously or heterogeneously and then charging them into the device. Osmotically effective solutes used for the former purpose include magnesium sulfate, magnesium chloride, sodium chloride, potassium chloride, potassium sulfate, sodium sulfate, lithium sulfate, potassium acid phosphate, d-mannitol, urea, inositol, magnesium succinate, tartaric acid, carbohydrates such as raffinos, sucrose, glucose, α-d-lactose monohydrate, mannitol, and mixtures thereof. The amount of osmagent in the blend with the osmopolymer usually is from 1% to 40%, or higher, with the total of all ingredients comprising the second composition equal to 100%. The osmotic pressure of an osmagent, or an osmopolymer, can be measured using an osmometer. An osmometer used for the present measurements is identified as Model 320B, Vapor Pressure Osmometer, manufactured by the Hewlett Packard Co., Avondale, Penna. Osmagents and osmopolymers are known to the art in U.S. Pat. Nos. 4,327,725 and 4,612,008.

Delivery device 10 can be manufactured by standard manufacturing techniques. In one process, wall 12 and liner 19 are independently injection molded, or extruded, and then assembled to produce liner 19 positioned inside wall 12. Then, the first composition is charged into the assembled article of manufacture, and the second composition next added thereto in layered arrangement. The ends are, optionally, heat sealed or plugged, or solvent/solute sealed, and at least one passageway is molded in place, is drilled or pre-formed in a closed state, to be broken open at the time of use through wall 12 to connect the first composition with the exterior of delivery device 10. Outer coat 21 can be applied by molding, spraying or dipping the device into a coat forming composition. Another technique that can be used for applying the coat is the air suspension procedure. This procedure consists of suspending and tumbling the manufacture in a current of air and a coat forming composition until the exterior coat is applied to the outside surface of wall 12. The air suspension procedure is described in U.S. Pat. Nos. 2,779,241; 4,327,725; in the *J. Am. Pharm. Assoc.*, Vol. 48, pp 451–59, (1979); ibid., Vol. 49, pp. 83–4, (1960). Other standard manufacturing procedures are described in *Modern Plastics Encyclopedia*, Vol. 46, pp 62–70, (1969), and in *Pharmaceutical Sciences*, by Remington, 14th Ed., pp 1626–78, supra.

Exemplary solvents suitable for manufacturing the wall and the coat include inorganic and organic solvents that do not adversely affect the wall forming material and the final device. The solvents broadly include members selected from the group consisting of aqueous solvents, alcohols, ketones, esters, ethers, aliphatic hydrocarbons, halogenated solvents, cycloaliphatic aeromatics, heterocyclic solvents and mixtures thereof. Typical solvents include acetone, diacetone alcohol, methanol, ethanol, isopropyl alcohol, butyl alcohol, methyl acetate, ethyl acetate, isopropyl alcohol, butyle alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol, and the like.

The expression, "exit means 13," as used herein, comprises means and methods suitable for the metered release of beneficial drug 15 from compartment 14 of dosage form 10. The means 13 includes at least one passageway, orifice, or the like, through wall 12 for communicating with compartment 14. The expression, "at least one passageway," includes aperture, orifice, bore, pore, porous element through which the drug can migrate, hollow fiber, capillary tube, porous overlay, porous insert, and the like. The expression also includes material that erodes or is leached from wall 12 in the fluid environment of use to produce at least one passageway in dosage form 10. Representative material suitable for forming at least one passageway, or a multiplicity of passageways, include an erodible poly(glycolic) acid or poly(lactic) acid member in the wall; a gelatinous filament; poly(vinyl alcohol); leachable materials such as fluid removable pore forming polysaccharides, salts, or oxides, and the like. The expression includes structural characteristics that concentrate stress at a precise point on wall 12 so that only a small amount of force will induce breakage of wall 12, yielding a passageway through wall 12, from compartment 14 to the outside of the device. A passageway or a plurality of passageways can be formed by leaching a material such as sorbitol from the wall. The passageway can have any shape such as round, triangular, square, elliptical, and the like, for assisting in the metered release of beneficial agent from dosage form 10. Dosage form 10 can be constructed with one or more passageways in spaced apart relations or more than a single surface of a dosage form. Passageways and equipment for forming passageways are disclosed in U.S. Pat. Nos. 3,845,770; 3,916,899; 4,063,064 and 4,008,864. Passageways formed by leaching are disclosed in U.S. Pat. Nos. 4,200,098 and 4,285,987.

DETAILED DESCRIPTION OF EXAMPLES

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE 1

A delivery system manufactured in the shape of a drug delivery device comprising a lead end with an exit passageway, and a distant closed end is manufactured as follows: first, a means designed as a liner is prepared by heating pellets of low density polyethylene, followed by extruding the hot polyethylene to produce a tube. The polyethylene is extruded neat, that is, free of any additives. Next, a rate controlling wall, shaped as a tube, is prepared from a wall forming composition comprising 28 g of cellulose acetae butyrate, 10 g of tributyl citrate, and 12 g of polymethyl methacrylate. The rate controlling wall is prepared by slowly adding 12 g of polymethyl methacrylate to a heated mixer, 170° C., and mixed for about 5 minutes to allow the polymer crystals to fuse together. Next, several drops of the tributyl citrate plasticizer are added to the mixer. Then about 5 g of the tributyl citrate is added to 28 g of cellulose acetate butyrate and the two ingredients mixed thoroughly into a homogeneous mixture. Next, the remainder of the tributyl citrate is added slowly to the polymethyl methacrylate, tributyl citrate in the mixer and the temperature of the mixer is lowered to 135° C. Next, the cellulose acetate butyrate, tributyl citrate blend is added to the mixer and the temperature raised to 190° C., to uniformly melt the cellulose acetate butyrate. After 5 minutes at this temperature, the temperature of the mixer is lowered to 100° C. and the mixing continued for 5 additional minutes. The mixer was cooled to room temperature and the wall forming composition cut into small pieces.

Next, the cut wall forming composition is fed into a turning extruder, about 8 rpm, and forced through the core passageway of the extruder. The composition melts at the temperature of the extruder and its die, about 140° C. to 150° C. The resultant rate controlling wall tubing measured approximately 0.176 inch outer diameter, 0.156 inch inside diameter, with a wall thickness of about 10 mils (0.256 mm).

The driving member composition is prepared from a composition comprising 670 g of sodium Carbomer ®, the sodium salt of polyacrylic acid, 290 g of sodium chloride, 40 g of polyvinyl pyrrolidone and 10 g of magnesium stearate by wet granulating with denatured ethanol in a 90:10 ratio with deionized water. Approximately 700 ml of granulation solvent is used for the wet granulation. Next, the wet granulation is passed through a 10 mesh screen and placed in a 50° C. oven and dried over night. After drying the granulation is removed from the oven and allowed to hydrate to approximately 9.3% water content. The granulation is passed again through a 10 mesh screen. After granulation 10.1 g of magnesium stearate is added and all the ingredients mixed for about 5 minutes. The resulting granulation is ready for use in the delivery device.

Next, the low density polyethylene liner and the rate controlling tubular shaped wall are cut to preselected device forming lengths. The rate controlling tubular wall is cut to a length of 1536±5 mils, and the protective liner cut to a length of 847± mils.

Then, 96 mg of the driving member composition is weighed out and compressed in a Carver ® laboratory press. The composition is pressed with a 5/32 inch round die with one end flat and the other end concave. The compressed composition is inserted into one end of the rate controlling tubular wall with the dome flush with the end of the wall.

Next, about 100 g of microcrystalline wax that forms the interface layer between the driving member composition and the drug with pharmaceutically acceptable composition is melted in a 72° C. forced air over to a molten state. Then a 10 cc glass syringe is filled with the molten wax and a layer 1.25 cm is deposited at the interface of the driving member composition. The wax is allowed to cool, and then tamped to assure a flat, even surface for receiving the beneficial drug with pharmaceutically acceptable carrier composition.

Next, the protective liner is inserted into the rate controlling tubular wall such that one end of the liner is inserted slightly into the wax layer to ensure a water tight seal, and the other end is flush with the top of the outer, rate controlling tubular wall, in a snug fit arrangement.

Then, the bottom of the delivery device, the area comprising the driving member composition, is sealed with a dilute slurry of cellulose acetate butyrate and methylene chloride. The bottom of the delivery device is dipped into the slurry and then dried overnight. This process completes the continuity of the semipermeable wall. Then, the top of the delivery device is closed with a cap, for example, a polycarbonate cap having an outside diameter equal to the inside diameter of the delivery device. The cap is solvent welded to the delivery device by dipping the cap into methylene chloride and then assemblying the delivery device. The solvent is allowed to evaporate overnight.

Next, the pharmaceutically acceptable carrier is prepared as follows: first, gelatin from porcine skin, having approximately 300 bloom, is passed through an air jet micropulverizer and then the gelatin is passed through a 200 mesh sieve. Then, 20.58 g of glycerol is charged into a beaker and 0.42 g of gelatin placed on top of the glycerol. The two ingredients are stirred for about ½ hour at room temperature. Next, 1.05 g of L-histidine is added to the mixture. Then, the mixture is heated at 60°-70° C. with constant stirring to yield a uniform blend. The heating and mixing is continued for about ½ hour. Finally, the mixture is allowed to cool to room temperature and form a gel.

Then, 13.3 g of the freshly prepared gel is added to 5.7 g of porcine somatotropin hormone and blended with a spatula. The hormone is added to the gel in small increments, with each increment added into the gel blended to yield the hormone formulation. The hormone formulation is injected through the cap into the delivery device onto the wax interface layer. The cap orifice is sealed by depositing drops of cellulose acetate butyrate in methylene chloride for forming a fluid tight delivery device. Finally, an exit passageway is drilled through the cap producing an orifice smaller in diameter than the orifice originally in the cap through which the filling was performed during manufacturing the device for delivering the beneficial drug to an animal.

EXAMPLE 2

Figure 6:
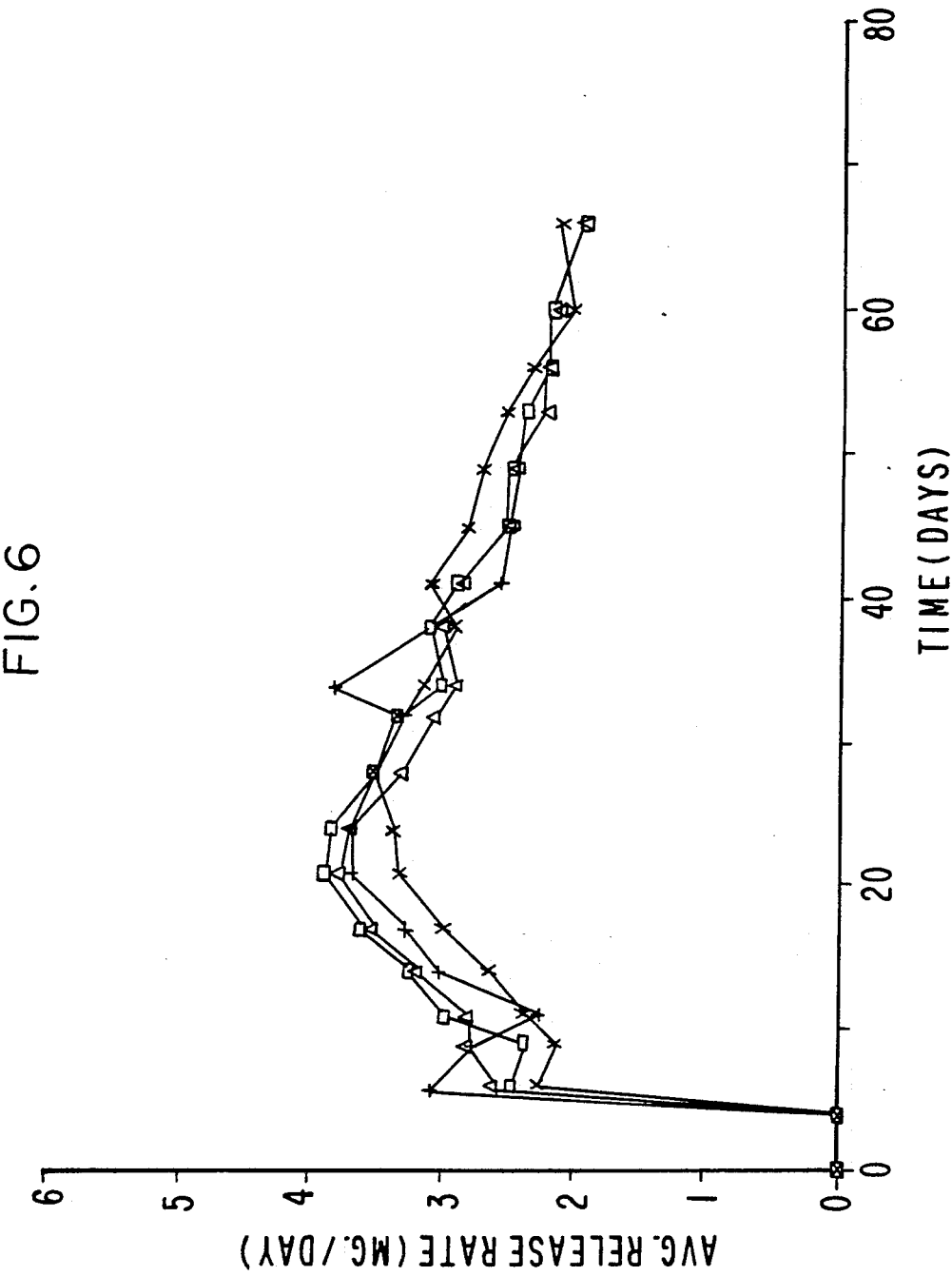
FIG. 6 is a graph illustrating the release patterns for a series of delivery devices provided by the invention.
Figure 7:
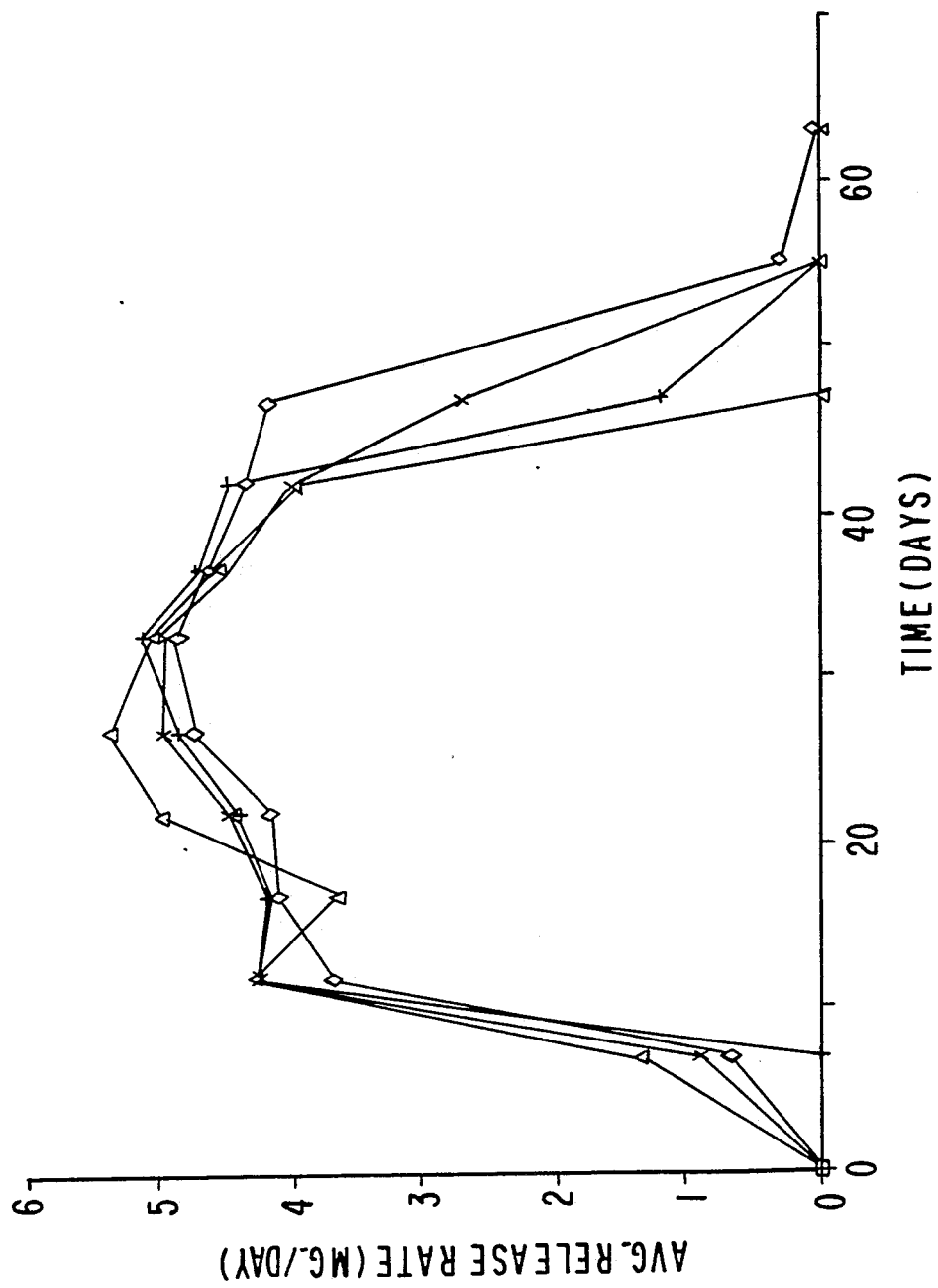

The manufacturing procedure set forth in Example 1 is followed in this example. In this example, delivery device 10 is coated with a semipermeable coat. The semipermeable coat is formed from a coat-forming composition comprising a 90:10 ratio of methylene chloride methanol solvent and 3% solids comprising 90% cellulose acetate butyrate and 10% tributyl citrate. The solvents are mixed and after mixing the cellulose acetate butyrate is added slowly followed by the tributyl citrate plasticizer. The coat forming composition is applied with an aeromatic coater, at a pump speed of 15-20 ml/minute, at an inlet temperature of 37° C. to apply a coat of 8-9 mils 0.204 to 0.206 mm) thick. Next, the coated delivery devices are cooled in a forced air over at 37° C. for 2-3 days to evaporate the solvents. Finally, an exit passageway is drilled through the cap for delivering the beneficial drug to the biological receptor. Accompanying FIG. 6 depicts the average release rate in milligrams per day for four delivery devices provided by the invention. The delivery device were made with means 19 for protecting the beneficial agent composition from unnecessary exposure to aqueous fluids. The release curves for the four different delivery devices are identified by a plus, square, triangle and multiplication sign. Accompanying FIG. 7 depicts the average release rate in milligrams per day for delivery devices made without means 19. The release curves for the delivery device are identified by plus, square, triangle and multiplication signs.

EXAMPLE 3

An embodiment of the invention pertains to a method for delivering a beneficial drug to an animal. The method comprises implanting a device shaped, sized and adapted as an implant into an animal; such as a muscle thereof. The method comprises the steps of: (A) admitting into an animal a delivery device comprising: (1) an outer wall comprising a semipermeable composition permeable to the passage of fluid and substantially impermeable to the passage of drug, the wall surrounding and forming: (2) an internal lumen; (3) liner means in the lumen in contact with the wall as an aid for governing the passage of an internal fluid into the compartment; (4) a layer of a composition comprising a beneficial drug and a pharmaceutically acceptable carrier in the lumen in contact with the liner means; a layer of a composition comprises means for delivering the beneficial drug in the compartment; (5) a layer comprising a composition substantially impermeable to the passage of fluid interposed between the layer comprising the beneficial drug and the layer comprising the driving means; (6) a coat comprising a composition permeable to the passage of fluid in contact with the exterior surface of the wall; and (7) at least one orifice in the device communicating with the lumen; (B) imbibing fluid through the wall and the coat for causing the driving means to expand and push against the composition comprising the drug; and (C) delivering the beneficial drug from the compartment by the expandable means continuously expanding at a controlled rate causing the composition comprising the beneficial drug to be delivered in a therapeutically effective amount through the orifice to the animal over a prolonged period of time.

The novel devices of this invention use means for the obtainment of precise release rates in the environment of use while simultaneously maintaining the integrity of the device. While there has been described and pointed out features of the invention as applied to presently preferred embodiments, those skilled in the art will appreciate that various modifications, changes, additions and omissions in the devices illustrated and described can be made without departing from the spirit of the invention.

We claim:

1. A device for delivering a beneficial agent to an environment of use, wherein the device comprises:

(a) a wall comprising in at least a part a composition permeable to the passage of aqueous fluid, which wall surrounds;
(b) an internal space;
(c) a beneficial agent in the internal space;
(d) a pharmaceutically acceptable carrier for the beneficial agent in the internal space;
(e) a liner comprising a composition substantially impermeable to the passage of aqueous fluid, said liner in the internal space that surrounds the area initially occupied by the beneficial agent for substantially preventing the passage of fluid into the internal space whereby the beneficial agent is substantially shielded from fluid contact;
(f) means in the internal space for displacing the beneficial agent from the device; and,
(g) means in the wall connecting the exterior of the device with the internal space for delivering the beneficial agent to the environment of use.

2. The device for delivering the beneficial agent to the environment of use according to claim 1, wherein the beneficial agent is a hormone.

3. The device for delivering the beneficial agent to the environment of use according to claim 1, wherein the device is an implant.

4. The device for delivering the beneficial agent to the environment of use according to claim 1, wherein the beneficial agent is somatotropin.

5. The device for delivering the beneficial agent to the environment of use according to claim 1, wherein the liner comprises a coat in contact with the inside wall, which coat substantially shields the beneficial agent from aqueous fluid contact.

6. The device for delivering the beneficial agent to the environment of use according to claim 1, wherein a layer comprising a composition substantially impermeable to the passage of aqueous fluid is between the beneficial agent and the means for displacing the beneficial agent.

7. The device for delivering the beneficial agent to the environment of use according to claim 1, wherein the device is adapted as an implant for livestock.

8. The device for delivering the beneficial agent to the environment of use according to claim 1, wherein the liner comprises a polycarbonate.

9. The device for delivering the beneficial agent to the environment of use according to claim 1, wherein the environment of use is a pig.

10. The device for delivering the beneficial agent to the environment of use according to claim 1, wherein histidine is present in the internal space.

* * * * *